United States Patent
Yoo (12)

(10) Patent No.: US 6,411,084 B1
(45) Date of Patent: Jun. 25, 2002

(54) MAGNETICALLY ACTIVATED WELL TOOL

(75) Inventor: Kwang M. Yoo, Houston, TX (US)

(73) Assignee: Halliburton Energy Services, Inc., Houston, TX (US)

(*) Notice: Subject to any disclaimer, the term of this patent is extended or adjusted under 35 U.S.C. 154(b) by 0 days.

(21) Appl. No.: 09/286,362

(22) Filed: Apr. 5, 1999

(51) Int. Cl.[7] .................. E21B 47/09; G01N 27/72; G01R 33/12
(52) U.S. Cl. ............... 324/221; 324/235; 166/255.1
(58) Field of Search .................. 324/219, 220, 324/221, 235, 239; 166/66.5, 255.1

(56) References Cited

U.S. PATENT DOCUMENTS

| 3,015,063 A | * 12/1961 | Ownby ................. 324/221 |
| 3,570,594 A | 3/1971 | Hamilton ............... 166/64 |
| 4,634,978 A | 1/1987 | Watanabe ............... 324/253 |
| 4,918,824 A | 4/1990 | Farrar .................. 33/361 |
| 5,251,170 A | 10/1993 | Daughton et al. ........ 365/158 |
| 5,329,269 A | 7/1994 | Watson ................. 336/213 |
| 5,361,838 A | 11/1994 | Kilgore ................ 166/255 |
| 5,420,819 A | 5/1995 | Pohm ................... 365/158 |
| 5,424,236 A | 6/1995 | Daughton et al. ........ 437/52 |
| 5,526,022 A | 6/1996 | Donahue et al. ......... 345/156 |
| 5,569,544 A | 10/1996 | Daughton ............... 428/611 |
| 5,595,830 A | 1/1997 | Daughton ............... 428/611 |
| 5,617,071 A | 4/1997 | Daughton ............... 338/32 R |
| 5,636,159 A | 6/1997 | Pohm ................... 365/158 |
| 5,720,345 A | * 2/1998 | Price et al. ........... 166/66.5 |
| 5,729,137 A | 3/1998 | Daughton et al. ........ 324/252 |
| 5,768,180 A | 6/1998 | Pohm ................... 365/158 |
| 5,831,426 A | 11/1998 | Black, Jr. et al. ...... 324/127 |

OTHER PUBLICATIONS

Halliburton Company; 3–1/4–Inch Universal CCL Tool (UCCL) Service Manual; No. 770.00494; May 1993; (pp. 47).

Nonvolatile Electronics, Inc.; Brochure; The New Leader in Magnetic Sensor Technology; May 1998; (p. 4).

* cited by examiner

Primary Examiner—Walter E. Snow
(74) Attorney, Agent, or Firm—Conley, Rose & Tayon, P.C.

(57) ABSTRACT

A casing joint locator device and methods of use are described. The locator device includes a giant magnetoresistive (GMR) sensor that is capable of detecting joints between sections of casing in a wellbore. The methods and devices described detect perturbations in the earth's magnetic field caused by air gaps and discontinuities associated with a casing joint or with an external casing joint collar. As a result, they are capable of detecting flush and standard collared joints. The casing joint locator generates essentially no magnetic or electromagnetic field so that other downhole instrumentation is not affected by its presence.

34 Claims, 7 Drawing Sheets

MAGNETICALLY ACTIVATED WELL TOOL

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The present invention relates to casing joint locator devices of the type used within wellbores. The invention also relates generally to devices and methods for detecting connections in strings of tubular members by sensing perturbations in natural magnetic fields induced within the string.

2. Description of the Related Art

Casing collar locators are used to locate joints within the borehole casing. The locator is suspended on a wireline cable and passed through the cased borehole. The locator device detects the collars used at joints in the casing string as the locator device is moved upwardly and/or downwardly through the casing. Sections of casing are typically joined by an exterior collar which secures the two adjacent ends of the casing section to one another in a threaded engagement. As the locator moves adjacent to a collar, it detects a change in the magnetic readings resulting from the increased exterior thickness of, or additional mass of metal associated with, the casing wall.

Casing collar locators are extremely important tools for downhole operations. They are virtually required for depth correction operations and for the accurate placement of downhole devices such as locks and packers. It is desired to avoid the location of a casing joint when setting a packer, for example, since the joint presents a gap or discontinuity in the casing wall that may prevent the packer's elastomeric sealing element from sealing properly at those locations.

In order to detect a casing collar, conventional casing collar locator devices typically rely on the generation of a relatively powerful magnetic field from the locator using either a permanent magnet or by passing a current through a coil to induce magnetism. A significant amount of power is required to generate the magnetic field. As the coil passes adjacent a collar in the casing, the flux density of the magnetic field is changed by the additional thickness of metal provided by the collar. The change causes an electrical output signal to be generated that indicates the presence of the collar, and this output signal is transmitted to the surface of the well through the wireline.

Unfortunately, conventional casing collar locator devices suffer from operational disadvantages and limitations of their effectiveness. Conventional locators are not greatly sensitive, in general, to changes in the wellbore casing. As a result, conventional casing collar locators are reliable only in a "dynamic" mode wherein the locator is moved rapidly through the wellbore casing in order to accurately detect the presence of collars. If the locator is moved too slowly, the changes in the signal indicative of the presence of the collar may be too gradual to be recognized by the well operator.

Dynamic location of collars is disadvantageous because it tends to provide less accurate real-time information concerning the position of the casing joint. For example, if it is desired to set a packer five feet below a particular casing joint collar in a wellbore, a conventional casing collar locator would be moved rapidly either upwardly or downwardly through the wellbore until the particular casing collar is detected. When that occurs, a signal is provided to the wellbore operator which indicates the location of the collar. Due to movement of the locator through the casing, however, the casing collar locator is no longer positioned proximate the collar by the time the operator receives the signal and reacts to it by stopping movement of the locator. The precise position of the collar must then be somewhat approximated given the current position of the locator within the wellbore.

Additionally, conventional locator devices locate casing joints by detecting a difference in thickness of the casing wall due to the presence of an external collar. These devices are actually, "collar" locators rather than "joint" locators. As a result, they are unable to reliably detect a "flush" joint wherein the casing wall thickness is not appreciably altered by the presence of the joint. A flush joint can occur where the adjacent casing sections are threaded directly to one another or where the collar is unusually thin or contains very little metal.

In addition, because conventional casing collar locators generate a significant magnetic field, they tend to interfere with other downhole instrumentation that rely upon accurate magnetic readings. For example, a compass-type magnetometer that is attempting to find magnetic north can be confused by the magnetic field generated by the casing collar locator. Some induction-type locators are known that generate and transmit strong electromagnetic waves, rather than magnetic fields, to detect casing collars. Unfortunately, these devices also tend to interfere with downhole instrumentation.

A need exists for a casing collar locator device that can more reliably detect the presence of casing section joints in a wellbore and flush joints that do not employ radially enlarged collars. Further, a need exists for a locator that generates a minimal or no magnetic field that would affect the operation of other downhole instrumentation.

SUMMARY OF THE INVENTION

The present invention provides an improved casing joint locator that is capable of reliably detecting joints between sections of casing in a wellbore. Methods and devices described herein sense perturbations, or changes, in magnetic fields that are induced in the casing sections by the earth's natural magnetic field. The induced magnetic fields include attractive forces that result from magnetic fringe effects proximate the longitudinal ends of the casing sections. The attractive forces are present at the connective joints of the casing string, thus presenting perturbations in the magnetic fields associated with the casing. Therefore, the inventive methods and devices will detect voids, such as air gaps and discontinuities, associated with a casing joint as well as the external collar associated with a standard collared joint. Thus, the inventive methods and devices are capable of detecting flush joints as well as more traditional joint arrangements.

The devices and methods described herein are also capable of providing clear and reliable signals indicative of the presence of flush joints wherein there is no appreciable change in the diameter of the casing at the joint. As a result, the possibility of a well operator failing to recognize such a signal is minimized.

The casing joint locator of the present invention generates essentially no magnetic or electromagnetic field. As a result, other downhole instrumentation is not affected by its presence. The locator device relies upon the earth's natural magnetic field to polarize and, thus, induce a magnetic field in the surrounding casing sections. Perturbations in this naturally-induced magnetic field, such as will result from the fringe effects associated with air gaps or discontinuities in the casing are detected by the locator device. The magnetic signature associated with the presence of a surrounding casing collar is also easily detected by the locator.

Further, methods and devices of the present invention provide for accurate measurement of lengths and distances, such as the length of casing joints or the distance between such joints.

The present invention also provides a locator device having a very small physical size and which uses very little power. Further, the locator device of the present invention does not need to be moved rapidly through the wellbore in order to reliably detect a casing joint. Thus, methods are described for "static" detection of casing joints wherein the locator is moved either very slowly or not at all, and the casing joint can still be reliably detected.

Thus, the present invention comprises a combination of features and advantages which enable it to overcome various problems of prior devices. The various characteristics described above, as sell as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENTS

Figure 1:
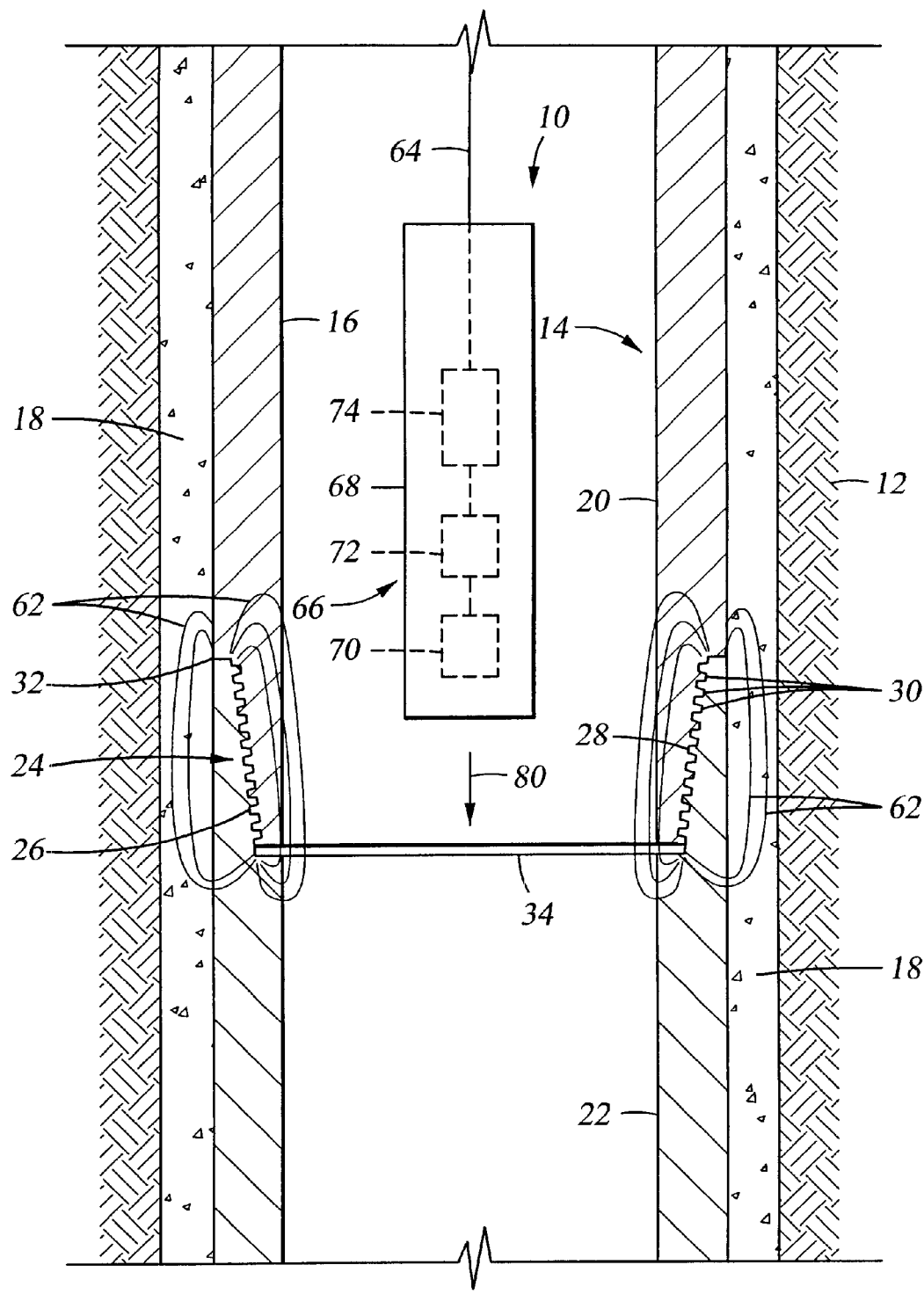
FIGS. 1–3 are cutaway side views of a pair of casing sections joined to one another by a flush joint and containing an exemplary casing joint locator constructed in accordance with the present invention.

Referring first to FIGS. 1–4, a borehole section 10 is depicted which is disposed through a formation 12 in the earth. The borehole section 10 includes a steel or metal tubular casing 14 that encloses and defines a bore 16 therethrough. The radial exterior of the casing 14 is surrounded by cement 18.

Figure 2:
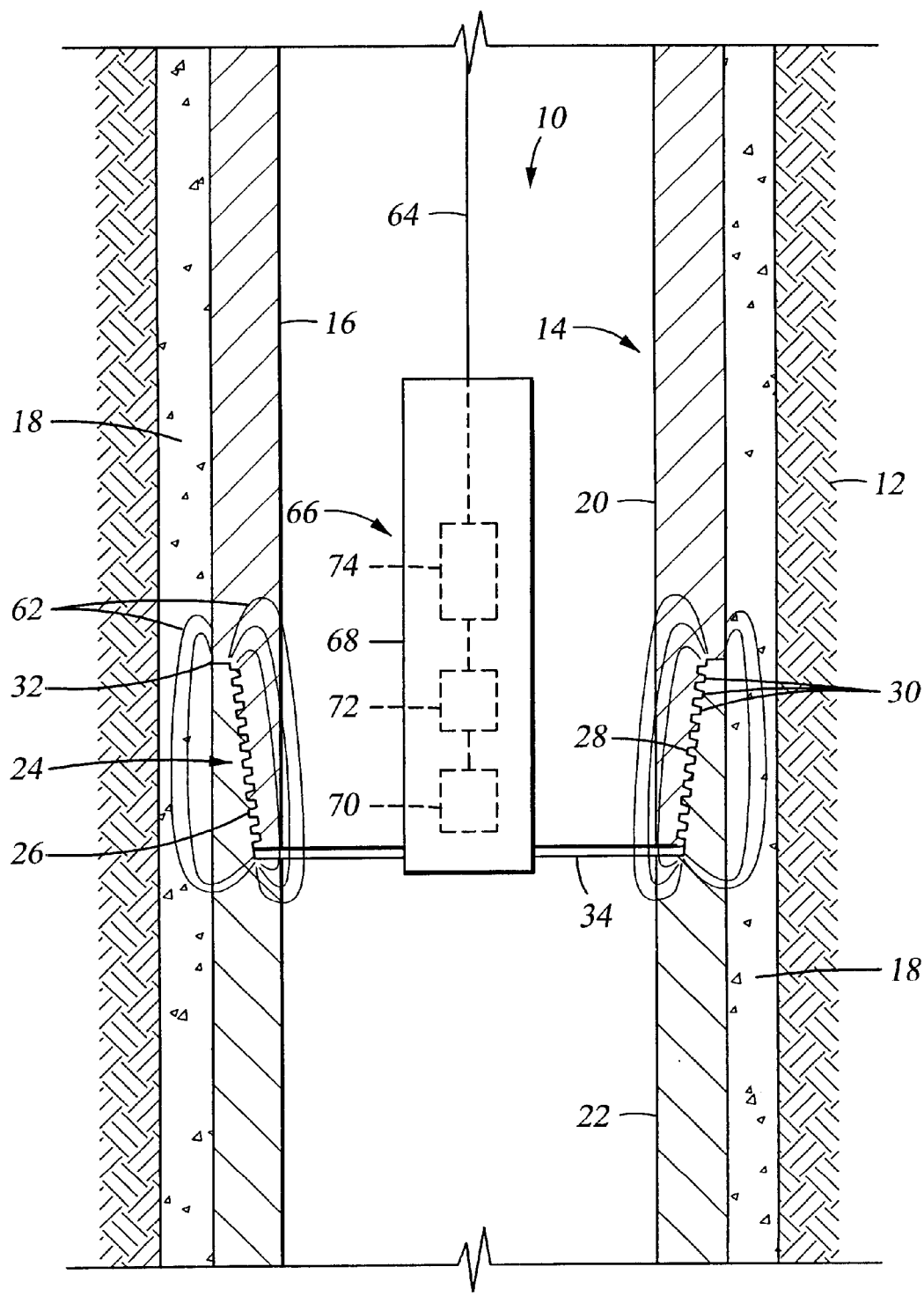
Figure 3:
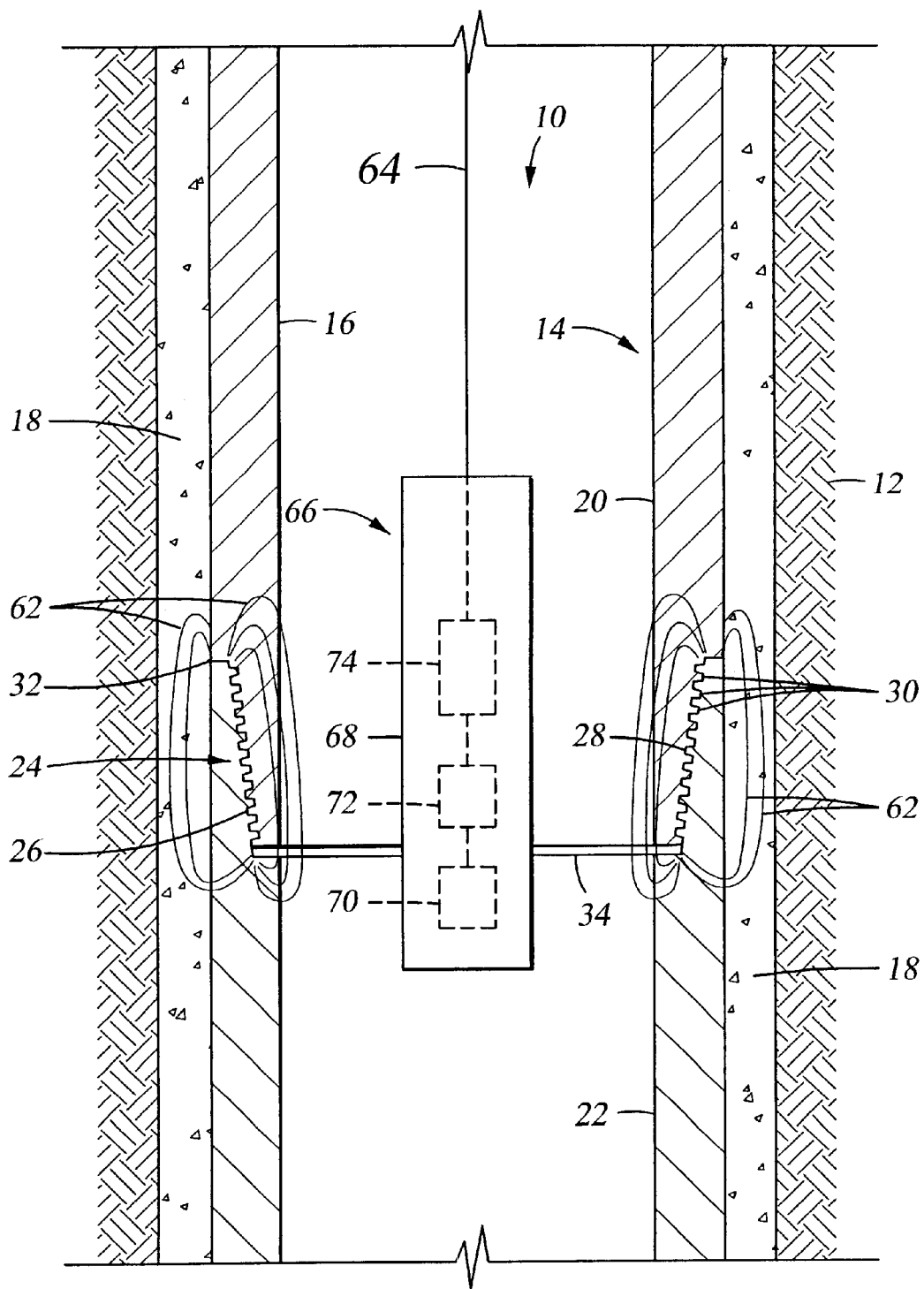

The casing 14 is made up of a plurality of elongated tubular casing sections. Two representative casing sections 20, 22 are shown affixed to one another at a threaded joint 24 that is shown in FIGS. 1–3 and in a closer view in FIG. 4. The joint 24 is made up of a pin type connector 26 on the upper casing section 20 which is secured within a complimentary box-type connector 28 on the lower casing section 22. The particular joint depicted in FIGS. 1–4 is a flush joint wherein there is no change in the thickness of the casing 14 at the joint. As is apparent, there is no external collar used to join the two casing sections.

Figure 4:
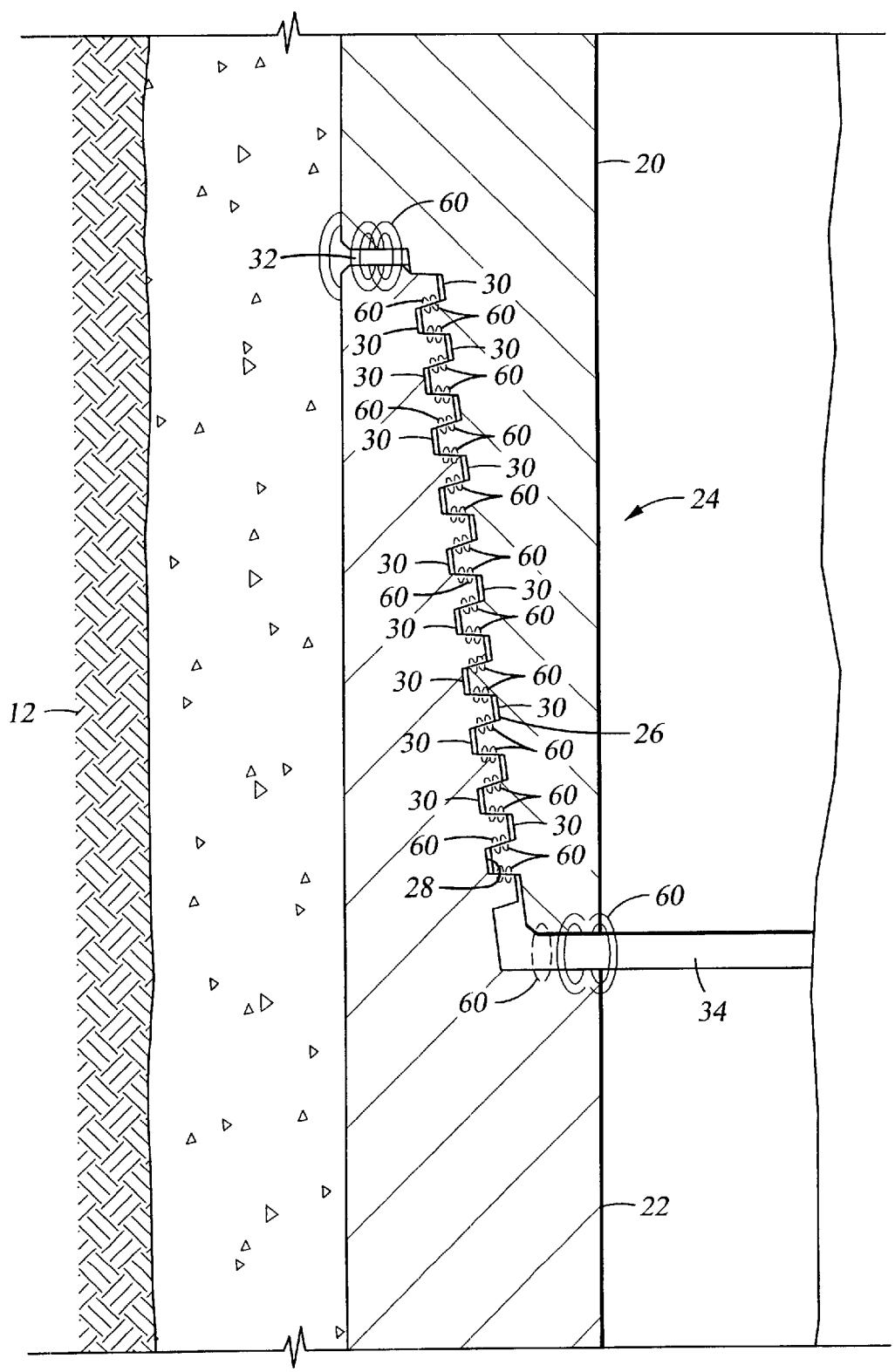
FIG. 4 is an enlarged view of a portion of a flush casing joint.

The threads of the joint 24 include a plurality of air gaps 30, best shown in FIG. 4, that are inherent in any such threaded connection where the generally complimentary threads of the two sections 20, 22 are interleaved. Further, discontinuities 32, 34 are present at either end of the threaded joint 24.

Figure 5:
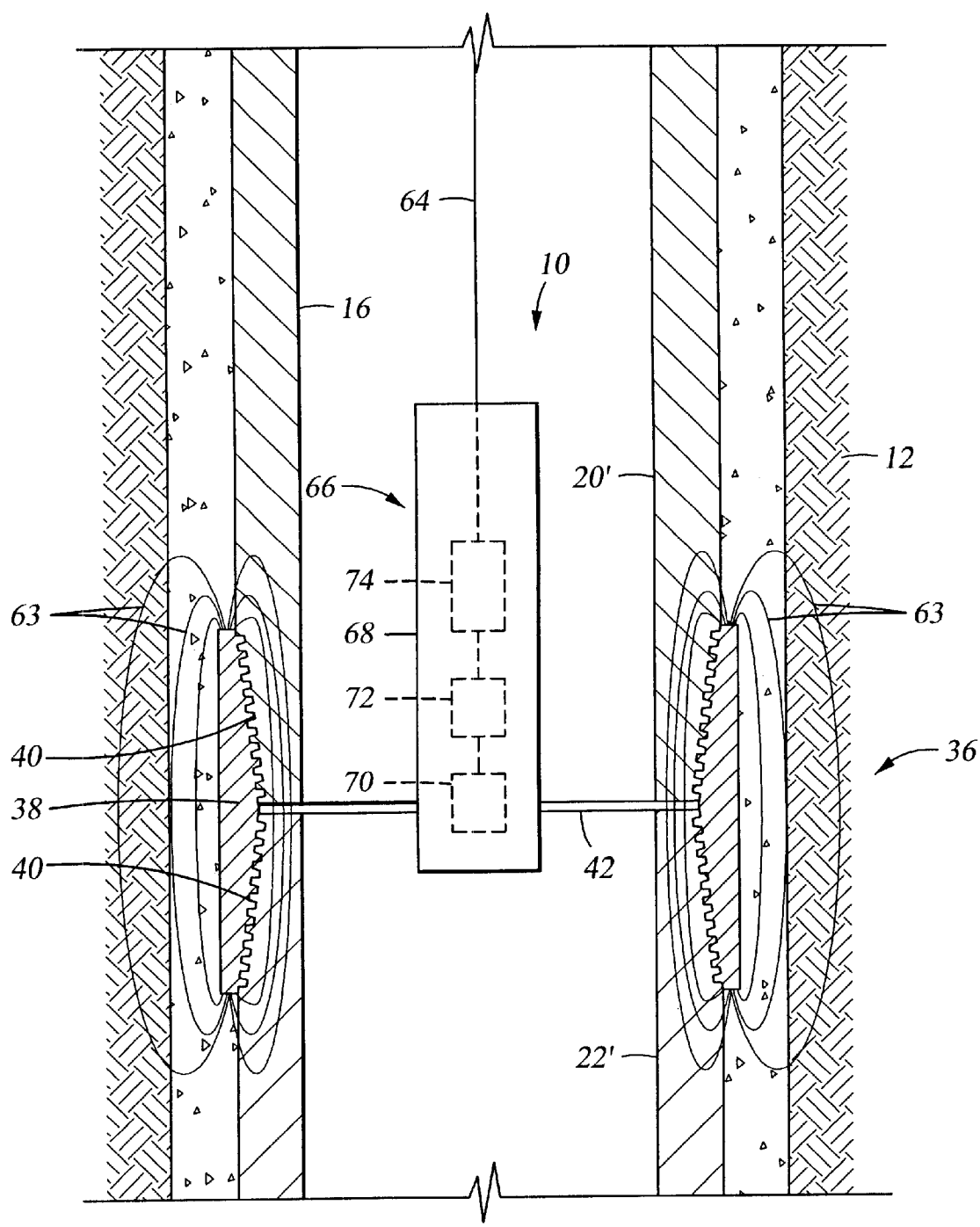
FIG. 5 is a cutaway side view of a pair of casing sections joined by an external collar connection and containing an exemplary casing joint locator constructed in accordance with the present invention.

FIG. 5 depicts a more standard collared joint 36 in which the pair of casing sections, designated as 20' and 22', are interconnected by a threaded collar 38 which is used to secure a pair of pin type connectors 40 therewithin. A discontinuity 42 is present between the two casing sections 20' and 22'.

Figure 6:
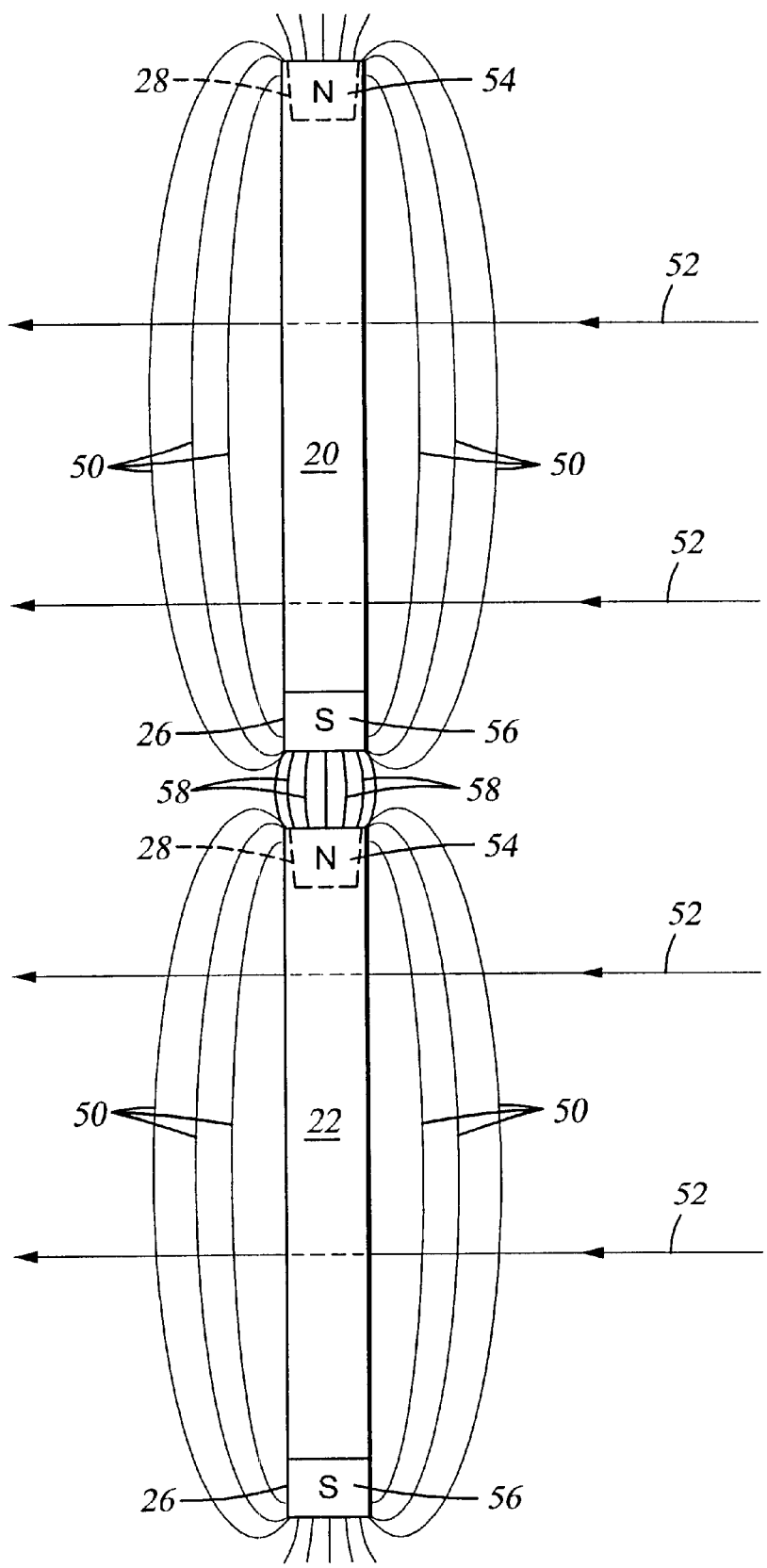
FIG. 6 illustrates the induction of magnetic forces in a pair of casing sections.

The inventor has recognized that the earth's natural magnetic field causes metallic casing sections to act as magnetic dipoles, thus providing their own naturally induced magnetic fields. Referring for the moment to FIG. 6, illustrative magnetic lines of force 50 are depicted around casing sections 20, 22 showing magnetic field that is induced within the casing sections 20, 22 by the earth's natural magnetic field 52, or the magnetic forces travelling from the magnetic north to south poles of the earth. As a practical matter, the induced magnetic field 52 is very weak, but it does exist, and is capable of being detected by suitably sensitive instrumentation. In essence, each section 20, 22 is polarized by the natural field 52 to act as a dipole providing attractive magnetic forces 50 running from their north poles 54 to their south poles 56. Each casing section 20, 22 is polarized in a common direction so that their north and south poles 54, 56 are commonly oriented. In addition, it should be understood that, when the casing sections are interconnected, the entire casing string thus formed will act as a single dipole to some extent, as well.

It is well known that the magnetic field is stronger proximate the north and south ends of a dipole. When the casing sections 20, 22 are placed close to one another in an end-to-end relation, as depicted in FIG. 6, there are attractive magnetic end effects, or "fringe effects," 58 which act between the two casing sections 20, 22. When the two casing sections 20, 22 are joined to one another via a threaded connection 24 (or 36), the fringe effects 58 continue to provide lines of attractive magnetic force between portions of the interconnected casing sections at and around the connection point. These lines of attractive force generally correspond to the presence of small gaps or separations between the two sections. By way of example, FIG. 4 is a close up view of a portion of the threaded flush joint connection 24 showing illustrative lines for these attractive forces 60 located at the gaps 26 and the discontinuities 28 and 29 for the connection. The aggregate of these small attractive forces 60 leads to an increased fringe effect magnetic signature 62 which is depicted by magnetic force lines in FIGS. 1–3.

An increase localized magnetic signature 63 is also shown to be associated with the collared joint 36 in FIG. 5. This signature 63 results from the increase mass of metal provided by the external collar 38 as well as the attractive magnetic effects associated with the discontinuity 42.

FIGS. 1–3 and 5 also show suspended within the bore 16 of the casing 14 a wireline 64 that is disposed into the wellbore 16 from the surface (not shown). The wireline 64 is adapted to transmit power and data in the form of a modulated electrical signal. It is preferred that the wireline 64 include power and ground wires, data transmission lines and command/response transmission lines. The wireline 64 also supports a detector assembly 66 that includes a pressure barrel 68 constructed of a non-magnetic material such as beryllium copper. The pressure barrel 68 is constructed to be resistant to fluids and capable of withstanding downhole pressures without collapsing.

The detector assembly 66 further includes a "giant magnetoresistive," or GMR magnetic field sensor 70 that is housed within the pressure barrel 68. GMR sensors are constructed from alternating, ultrathin layers of magnetic and non-magnetic materials. GMR sensors provide high sensitivity to changes in a nearby or surrounding magnetic field. GMR sensors of this type are currently manufactured and marketed by Nonvolatile Electronics, Inc., 11409 Valley View Road, Eden Prairie, Minn. 55344-3617, (612) 829-9217. The GMR sensor is adapted to detect a change in a surrounding magnetic field and, in response, thereto, generate a signal indicative of the change. The sensitivity of the GMR sensor permits detection of small voids in the surrounding magnetic structure, such as the air gaps 30 and the discontinuities 32, 34 of the casing joint 24. As a result, joints between a pair of interconnected casing sections can be detected by the detector assembly 66. It is noted that a GMR sensor itself generates essentially no magnetic signature and, therefore, will not affect the operation of other downhole equipment which detect or rely upon magnetic readings.

The detector assembly 66 also includes a signal processor 72 that is operably interconnected with the sensor 70. The signal processor 72 receives the signal provided by the sensor 70, amplifies the signal and shapes it in order to provide a more recognizable processed signal. In the preferred embodiment described here, the processed signal features a readily recognizable square wave, the high state portion of which corresponds to the presence of a joint. The signal processor 72 includes an amplifier and an analog-to-digital converter (neither shown), which are well-known components. The amplifier enhances the signal while the converter is used to convert the analog readings obtained by the sensor 70 into a more readily recognizable digital signal. If desired, the signal processor 72 may incorporate one or more noise filters of a type known in the art in order to remove noise from the signal generated by the sensor 70. Other signal processing techniques used to enhance the quality of such signals may be applied.

The detector assembly 66 further includes a data transmitter 74 that is operably interconnected with the signal processor 72. The data transmitter 74 receives the amplified and processed signal created by the signal processor 72 and transmits it to a distant receiver, typically located at the surface of the wellbore that includes borehole section 10. The distant receiver might comprise an oscilloscope, computer or storage medium for the signals.

In operation, the sensor 70 senses the perturbation provided by the increased or changed magnetic fields associated with the connections or joints between casing sections 20, 22 or 20', 22'. In the case of the collared connection 36 shown in FIG. 5, the sensor 70 senses the increased magnetic field in the surrounding casing resulting from the presence of the external collar 38 as well as that provided by the discontinuity 42.

Figure 7:
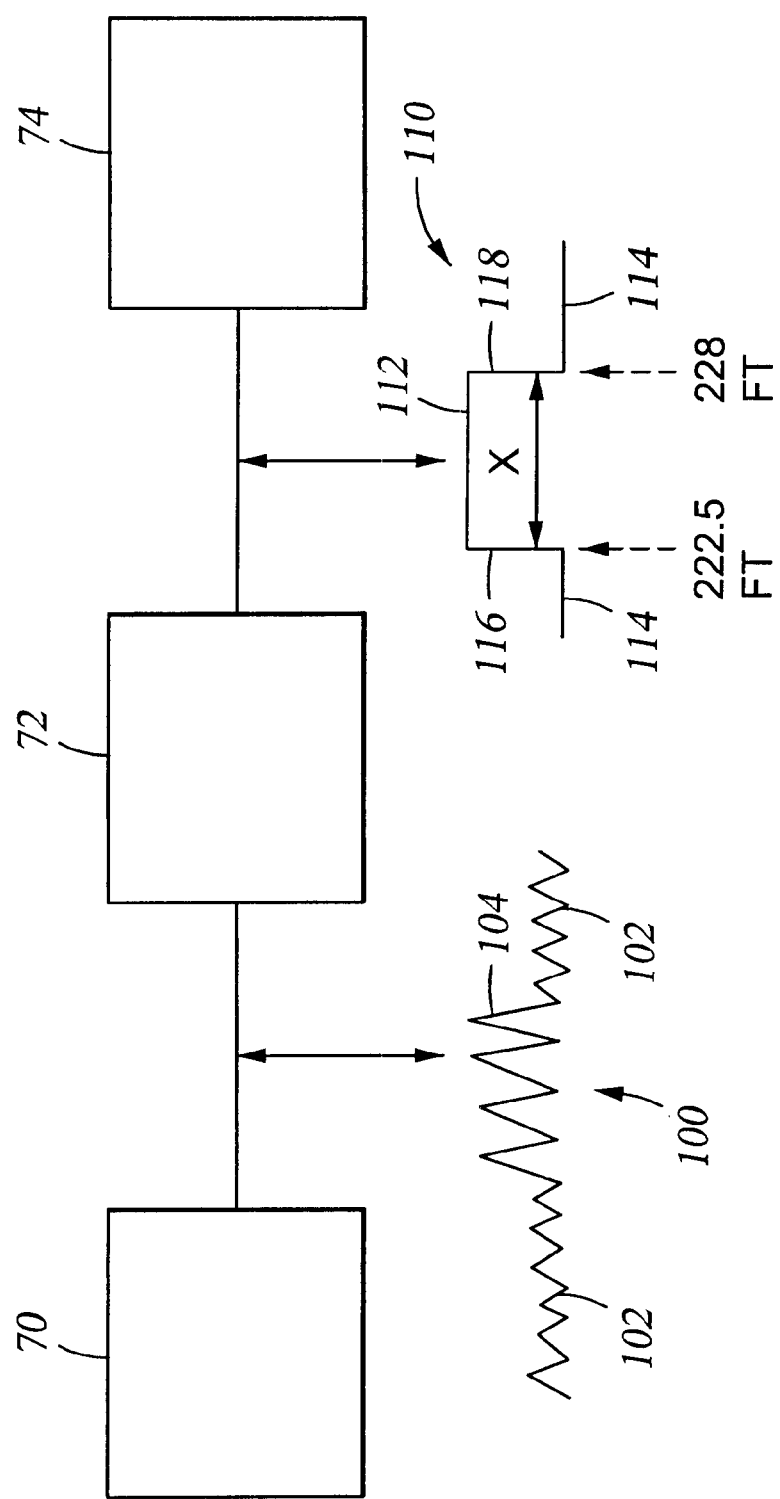
FIG. 7 is a schematic diagram illustrating exemplary signals received and generated by the signal processor.

FIG. 7 illustrates processing of the signals by the signal processor 72. An analog signal 100 is received by the processor 72 from the sensor 70. As shown, the analog signal 100 is made up of a number of peaks and valleys that correspond to changes in the magnetic field sensed by the sensor 70. The analog signal 100 includes a reduced baseline signal portion 102 that corresponds to detection by the sensor 70 of plain casing walls. The signal 100 also includes an enhanced signal portion 104 that corresponds to the detection by the sensor 70 of discontinuities or air gaps within surrounding casing walls. The enhanced signal portion 104 is significantly different from the baseline signal portion 102 due to changes in the borehole magnetic flux as a result of the discontinuities 32, 34 and air gaps 30 present in the casing 14. As noted, the signal processor 72 contains an amplifier and analog-to-digital converter, both of which are well-known components. The signal processor 38, therefore, produces a processed digital signal 110 based upon the analog signal 100 it receives. The processed signal 110 is preferably a square wave which is made up of "high" and "low" states, each of which are indicative of a different condition. This type of signal is preferred because it provides a more definite indication of condition than an analog signal such as signal 100. The high state portion 112 of the signal 100 is indicative of the presence of discontinuities and/or air gaps in the surrounding borehole wall and is produced when the sensor 70 is located adjacent a casing joint, such as joint 24. Conversely, a low state portion 114 results when there is an absence of such discontinuities and gaps. The processed signal 110 is received by and then transmitted to the surface via the data transmitter 74 on a periodic basis, such as every 50 milliseconds.

As explained, the high state portion 112 of the square wave of the processed signal 110 corresponds to the presence of discontinuities and/or air gaps in the surrounding casing wall while the low state portion 114 of the signal 110 indicates the absence of discontinuities and gaps that would affect the surrounding magnetic field. As a result, the length, ("x" in FIG. 5) of the high state portion 112 corresponds to the length of the joint 24 as measured from the upper discontinuity 32 to the lower discontinuity 34. The invention permits the length of the joint 24 to be determined from the length "x" of the high state portion 112 of the signal 110. This capability provides well operators with greater information regarding the exact location and sizes of joints within a wellbore and is, therefore, quite valuable. More specifically, the locator device 66 is typically moved at a relatively constant rate, or velocity, through the wellbore 10. This rate is known and controlled by the well operator. When this is the case, the locator device 66 is initially positioned at a known depth or location in the wellbore. If the initial position for the locator device 66 is at the surface of the well, the initial position will be at zero (0) feet. As the locator device 66 is lowered though the wellbore, the signal 110 is normally provided to the surface of the well, or updated, in a periodic fashion, i.e., every 50 milliseconds, over time. Because the velocity of movement (v) of the locator device 66 through the wellbore is known and the time (t) of signals is known, the location of the locator device 66 within the well can be determined. Further, the location of the locator device 66 can be referenced to the presence of a joint between casing sections so that the location of these joints is easily tracked and determined. Additionally, the signal length ("x") mentioned earlier can be easily correlated to the length of such a joint so that the actual length of the joint as well as the exact depth of portions of the joint can be determined.

The example is further illustrated in FIG. 7 where the analog signal 100 changes from its baseline signal 102 to the enhanced signal 104 upon encountering the leading portion of a joint, such as the upper discontinuity 32 of joint 24. The signal processor 72 converts the analog signal to processed signal 110 and, when the leading portion of the joint 24 is detected by the sensor 70, the processed signal 110 changes from a low state signal 114 to a high state signal 112 at point 116. At the surface, point 116 is correlated with a depth marker (e.g., 222.5 ft.), as calculated by the velocity vs. time relationship described earlier. Such correlation can be easily accomplished using known software of calculations. As the sensor 70 is moved downwardly and past the lower portion of the joint 24, the processed signal 110 changes from a high state signal 112 to a low state signal 114 at point 118. Point 118 is also correlated with a depth marker (e.g., 228 ft.). The difference between points 116 and 118 yields 5.5 ft., the length of the joint 24.

Operation of the detector assembly 66 in an exemplary wellbore is illustrated by the sequence of FIGS. 1–3 which show the detector assembly 66 being lowered through the borehole section 10. In FIG. 1, the detector assembly 66 is located within the borehole section 10 and moved in the direction of arrow 80 until the sensor 70 is substantially adjacent the discontinuity 32 at the upper end of the joint 24. At this point, the discontinuity 32 is detected by the sensor 70 and a processed signal 110 is moved to a high state 112 from a low state 114.

In FIG. 2, the sensor 70 is located proximate the air gaps 30 of the joint 24. As a result, the processed signal 110 will be maintained in the high state 112 due to the alteration in the surrounding magnetic field caused by these gaps 30. In FIG. 3, the detector assembly 66 has been moved downwardly to the point where the sensor 70 is disposed below the lower discontinuity 34 and is adjacent the wall of the lower casing section 22. Due to the absence of air gaps 30 or discontinuities 32, 34, the processed signal 110 will return to the low state 114.

It is noted that the detector assembly 66 of the present invention is also useful for detecting breaks or ruptures in the wall of the casing 14. Such breaks and ruptures also result in a change, or perturbation in the induced magnetic fields of casing sections. As a result, the detector assembly 66 is useful for finding damage within a wellbore casing. The methods of detecting such damage are substantially the same as those described above with respect to detecting casing joints.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. A method of locating a joint between a pair of tubular members each having a naturally induced magnetic field, comprising the operation of detecting a region substantially free of the magnetic fields of each tubular member, the region being caused by a fringe effect associated with the naturally induced magnetic field, the region being indicative of a void associated with the joint.

2. The method of claim 1 wherein the region substantially free of the naturally induced magnetic fields is detected by positioning a sensor proximate the void, the sensor being configured to detect the region substantially free of the naturally induced magnetic fields.

3. The method of claim 2 wherein the sensor is positioned proximate the void by disposing it through a tubular member using a wireline that is adapted to transmit electrical power.

4. The method of claim 1 further comprising the operation of generating a signal from the sensor, the signal being associated with the void.

5. The method of claim 4 further comprising the operation of amplifying the signal.

6. The method of claim 4 further comprising converting the signal to a processed digital signal.

7. The method of claim 6 wherein the processed digital signal comprises a square wave.

8. The method of claim 4 further comprising the operation of transmitting the signal to a remote receiver.

9. A casing joint locator assembly for use in a metal tubular having a plurality of sections, each of the sections having a unique magnetic field, the sections separated by spaced-apart axial gaps each forming a naturally induced magnetic signature, comprising a magnetoresistive field sensor adapted to be disposed within the metal tubular and to detect a region substantially free of the unique magnetic field of each section.

10. The casing joint locator assembly of claim 9 further comprising a signal processor operably interconnected with the sensor to generate a processed signal indicative of a region substantially free of the unique magnetic field of each section.

11. The casing joint locator assembly of claim 9 further comprising a means for receiving a signal generated by the signal generator and transmitting it to a remote location.

12. The casing joint locator assembly of claim 10 wherein the signal processor comprises an amplifier.

13. The casing joint locator assembly of claim 10 wherein the signal processor comprises an analog-to-digital converter.

14. The casing joint locator assembly of claim 10 wherein the signal processor comprises a noise filter.

15. The casing joint locator assembly of claim 9 further comprising a pressure barrel housing that substantially encloses the magnetoresistive sensor.

16. The casing joint locator assembly of claim 15 wherein the pressure barrel housing is substantially comprised of a non-magnetic material.

17. The casing joint locator of claim 16 wherein the non-magnetic material comprises beryllium copper.

18. A method of detecting one or more voids in the wall of a tubular member having a first magnetic signature being attributable to a naturally induced magnetic flux, comprising:

a) disposing a magnetoresistive sensor within a tubular member;

b) generating a signal from the sensor corresponding to the first magnetic signature;

c) moving the sensor proximate a void in the wall of the tubular member; and d) causing a change in the signal indicative of the presence of the void, the change being attributable to fringe effect.

19. The method of claim 18 further comprising the operation of transmitting the signal to a remote receiver.

20. The method of claim 18 further comprising the operation of processing the signal to obtain a more recognizable processed signal.

21. A method of detecting an increase in an amplitude of a magnetic field associated with fringe effects in a naturally induced magnetic field within a string of tubular members, the method comprising:

a) disposing a sensor proximate a string of tubular members having the naturally induced magnetic field; and b) sensing the increase in the amplitude of the naturally induced magnetic field with the sensor, the increase in the amplitude being caused by a fringe effect indicative of the attraction between a pair of dipoles disposed in an end-to-end relation.

22. The method of claim 21 wherein the magnetic field in the string of tubular members is induced by the earth's natural magnetic fields.

23. The method of claim 21 further comprising the operation of generating a signal indicative of the increase in the amplitude of the induced field.

24. The method of claim 23 further comprising the operation of transmitting the signal to a remote location.

25. A method of detecting perturbations in a naturally induced magnetic field within a string of tubular members, the method comprising:
   a) disposing a sensor proximate a string of tubular members having the naturally induced magnetic field;
   b) sensing a perturbation in the naturally induced magnetic field with the sensor, the perturbation being caused by a fringe effect indicative of the attraction between a pair of dipoles disposed in an end-to-end relation; and
   wherein the operation of sensing a perturbation comprises sensing an increased magnetic field indicative of the presence of an attachment collar for a pair of tubular members.

26. A well tool for detecting a gap in a naturally induced magnetic field, comprising:
   a pressure barrel; and
   a sensor disposed within said pressure barrel and adapted to generate a signal when exposed to the naturally induced magnetic signature field that is caused by fringe effect, said sensor being itself substantially free of a magnetic signature.

27. The well tool of claim 26 further comprising a signal processor associated with said sensor, said signal processor configured to convert said signal into digital data.

28. The well tool of claim 26 wherein said sensor is a giant magnetoresistive sensor operatively connected to a wireline adapted to convey signals, said sensor being adapted to transmit a signal through said wireline when exposed to the naturally induced magnetic signature.

29. A method of determining the length of a tubular disposed in a well bore, the tubular having a plurality of naturally induced magnetic signatures associated with fringe effects that occur at the tubular ends, the method comprising:
   detecting a plurality of naturally induced magnetic signatures associated with fringe effects indicative of connections in the tubular;
   associating each said naturally induced magnetic signature with a high state;
   calculating the intervals between successive high states; and converting the intervals to length measurements.

30. The method of claim 28 wherein the detecting step is performed at a relatively constant velocity; the calculating step is accomplished by measuring the time between signals; and the converting step is accomplished by correlating the velocity and time measurements with the high states.

31. The casing joint locator of claim 9 wherein said sensor is substantially non-magnetic.

32. The method of claim 1 further comprising minimizing any magnetic field associated with the sensor.

33. A method of detecting perturbations in a naturally induced magnetic field within a string of tubular members, the method comprising:
   a) disposing a sensor proximate a string of tubular members having the naturally induced magnetic field;
   b) sensing a perturbation in the naturally induced magnetic field with the sensor, the perturbation being caused by a fringe effect indicative of the attraction between a pair of dipoles disposed in an end-to-end relation; and
   c) negating any magnetic field associated with the sensor.

34. The method of claim 18 further comprising maintaining a magnetic-free area proximate to the sensor.

* * * * *